United States Patent [19]

Capuano, Sr. et al.

[11] Patent Number: 4,790,312
[45] Date of Patent: Dec. 13, 1988

[54] SURGICAL KNIFE

[75] Inventors: Francis A. Capuano, Sr., Stoneham; Vincent J. Piraino, Belmont, both of Mass.

[73] Assignee: Becton Dickinson Acutecare, Inc., Waltham, Mass.

[21] Appl. No.: 5,039

[22] Filed: Jan. 20, 1987

[51] Int. Cl.⁴ ............................................. A61B 17/32
[52] U.S. Cl. ..................................................... 128/305
[58] Field of Search ............... 128/753, 754, 751, 305, 128/354, 321; 30/162

[56] References Cited

U.S. PATENT DOCUMENTS

| | | |
|---|---|---|
| 651,395 | 6/1900 | Stapp . |
| 1,755,535 | 4/1930 | Bratrud ............................ 30/162 X |
| 2,483,750 | 10/1949 | Bratrud . |
| 2,941,511 | 6/1960 | Cieremans . |
| 2,968,489 | 1/1961 | Doniger . |
| 3,762,416 | 10/1973 | Moss et al. ........................... 128/305 |
| 3,776,237 | 12/1973 | Hill et al. . |
| 3,902,498 | 9/1975 | Niederer . |
| 3,906,626 | 9/1975 | Riuli . |
| 3,945,375 | 3/1976 | Banko . |
| 3,994,297 | 11/1976 | Kopf . |
| 4,002,366 | 1/1977 | Hammes . |
| 4,089,112 | 5/1978 | Richards . |
| 4,414,974 | 12/1983 | Dotson et al. . |
| 4,444,184 | 4/1984 | Oretorp ............................... 128/305 |
| 4,473,076 | 9/1984 | Williams et al. . |
| 4,491,132 | 1/1985 | Aikins . |
| 4,497,320 | 2/1918 | Nicholson et al. . |
| 4,523,379 | 6/1985 | Osterhout et al. . |
| 4,573,448 | 3/1986 | Kambin . |
| 4,576,164 | 3/1986 | Richeson . |
| 4,601,710 | 7/1986 | Moll ................................. 128/305 X |

FOREIGN PATENT DOCUMENTS 2091624 8/1982 United Kingdom ................ 128/321
2113550 8/1983 United Kingdom ................ 128/305

OTHER PUBLICATIONS

"Orthopaedic Blades", *Rudolph Beaver, Inc.* (Commercial Literature).
"Thackray Arthroscopy, Dandy Operative Instruments 4".
"Retractable Cannulated System", *Brimfield Scientific Instruments* Commercial Literature.
"Stille Arthroscopy Instrumentation", (Commercial Literature).
"New 3M Sheathed Knives", 3M, (Commercial Literature).

*Primary Examiner*—Michael H. Thaler

[57] ABSTRACT

A surgical instrument for operating percutaneously in a living body includes an elongated hollow handle, a shaft with a proximal portion extending within and secured, during use, to the handle and a distal portion extending distally of the handle, a cutting device, e.g., a surgical blade, fixedly supported during use by the distal end of the shaft, and a slidable tubular sheath having a distal portion extending distally of the handle, about the shaft, to the region of the blade. The sheath is sized and constructed for introduction into the living body through a puncture opening in its flesh. The instrument includes a mechanism, e.g., a sliding or rotating actuation knob, for moving the sheath axially relative to the handle between a first position in which the distal portion of the sheath surrounds the blade enabling safe positioning of the instrument in the body without cutting, and a second, retracted position exposing the blade. The position of the blade relative to the handle is fixed during movement of the sheath.

9 Claims, 1 Drawing Sheet

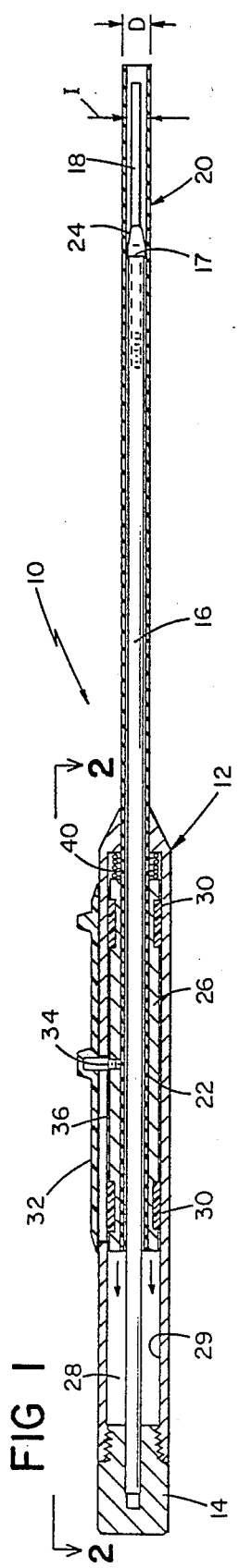
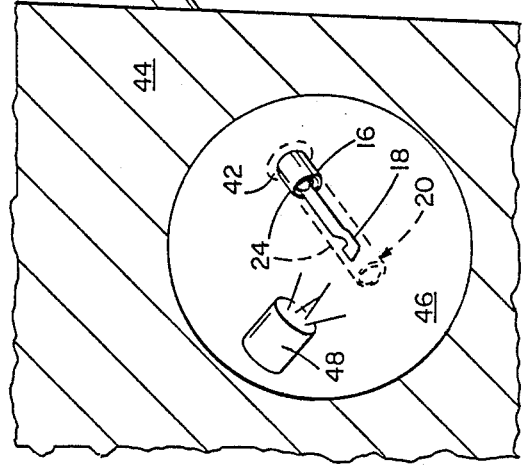
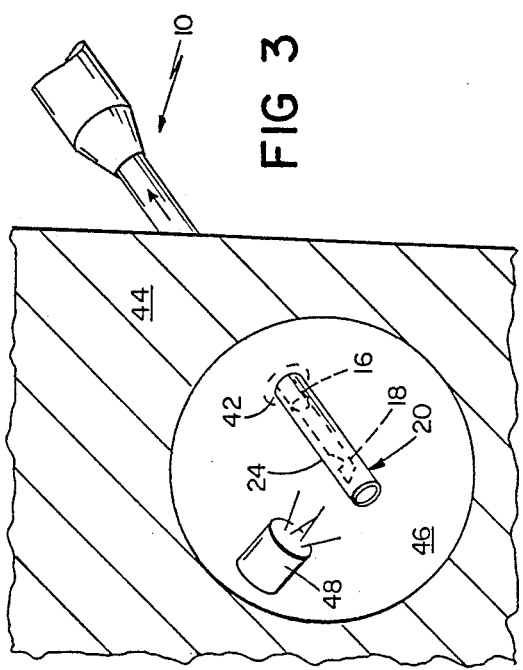
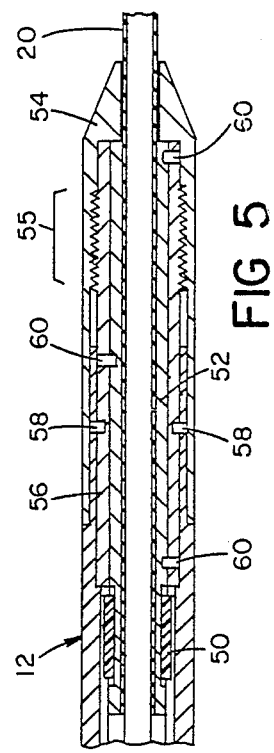
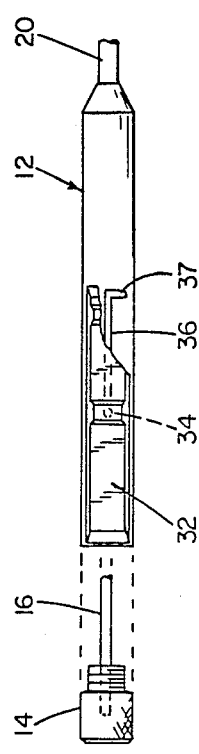

SURGICAL KNIFE

BACKGROUND OF THE INVENTION

The invention relates to surgical knives for percutaneous use.

The desire to perform procedures least invasively, i.e., with a minimum degree of opening the body, has led to percutaneous surgery in which the surgical knife is manipulated through a puncture opening, under visual guidance of an endoscope. Arthroscopic surgery of the knee is a common example of such surgery. Typically, the knife is introduced through a cannula to avoid unwanted cutting during introduction of the blade through the flesh. In some instances, the surgeon removes the cannula after the knife is introduced; in others, the cannula is left in place. An example of the latter is Oretorp, U.S. Pat. No. 4,444,184, a surgical instrument which combines an elongated tube and a blade which is projected axially out of the tube after introduction of the instrument through the flesh.

SUMMARY OF THE INVENTION

According to the invention, a surgical instrument for operating percutaneously in a living body comprises an elongated hollow handle, a shaft having a proximal portion extending within and secured, during use, to the handle and a distal portion extending distally of the handle, surgical cutting means fixedly supported during use by the distal end of the shaft, a slidable tubular sheath having a distal portion extending distally of the handle, about the shaft, to the region of the cutting means, the sheath sized and constructed for introduction into the living body through a puncture opening in its flesh, and means for moving the sheath axially relative to the handle between a first position in which the distal portion of the sheath surrounds the cutting means, enabling safe positioning of the instrument in the body without cutting, and a second, retracted position exposing the surgical cutting means, the position of the cutting means relative to the handle being fixed during such movement of the sheath.

Preferred embodiments have the following features. The instrument comprises a proximal cap removably connected to the handle, and the sheath and handle define an elongated passage extending axially the length of the instrument, the shaft and cutting means being sized relative to the passage through the sheath and handle whereby, upon disassembly of the cap from the handle. The shaft and blade are adapted for removal proximally through the passage, while the sheath remains in the puncture opening in the flesh of the living body. The means for moving the sheath axially relative to the handle comprises a knob disposed for movement along the outer surface of the handle, and engagement means extending through the handle into fixed engagement with the proximal portion of the sheath disposed within the handle, whereby movement of the knob along the handle outer surface results in movement of the sheath between first and second positions. The means for moving the sheath axially relative to the handle further comprises a sleeve sized and constructed for axial sliding movement within the handle, the distal portion of the sheath being fixedly connected to the sleeve, and the engagement means being disposed in a slot defined through the handle, between fixed connection to the knob and to the sleeve. The knob is disposed to slide generally axially along the outer surface of the handle, or, alternatively, the knob comprises an annular ring disposed to rotate about the handle. The instrument further comprises means for positively retaining the sheath in the first position surrounding the cutting means. The outer diameter of the sheath is of the order of about 4 mm, and the inner diameter of the sheath is of the order of about 3 mm, and the cutting means and shaft are sized for passage therethrough. The sheath has a proximal portion slidably disposed within the handle.

There is thus provided by the invention a surgical instrument for percutaneous use having a blade held in fixed position relative to the handle, and a sheath which is movable between a first position surrounding the blade to prevent unwanted cutting and a second position exposing the blade. The surgeon is able to position and then expose the blade, by movement of the sheath, without movement of the blade. Furthermore, the blade and shaft can be removed through the instrument while it remains in place within the body.

Other features and advantages of the invention will be understood from the following description of a presently preferred embodiment, and from the claims.

Preferred Embodiment

We first briefly describe the drawings.

DRAWINGS

FIG. 1 is a side section view of the surgical instrument of the invention;

FIG. 2 is a plan view, partially in section, of the instrument taken generally on the line 2—2 of FIG. 1;

FIGS. 3 and 4 are somewhat diagrammatic representations of the instrument inserted percutaneously into a cavity of a living body, under endoscopic guidance; and FIG. 5 is a side section view of an alternate embodiment of the surgical instrument.

In FIG. 1, the surgical instrument 10 consists of a hollow, elongated handle 12, terminating proximally in a cap 14 attached to the handle, e.g., by threading. An elongated shaft 16 is secured to the handle by press-fit into cap 14. The shaft extends distally of the handle to support a surgical cutting blade 18, e.g., the end of the shaft may of construction suitable for use with AR-THRO-LOK® blades of the type sold by Rudolph Beaver, Inc., of Waltham, Mass., described in U.S. Pat. No. 4,497,320, the disclosure of which is incorporated herein by reference. A tubular sheath 20 has a proximal portion 22 slidably disposed within the handle and a distal portion 24 extending distally of the handle, about the shaft to the region of the blade 18. The sheath has an outer diameter, D, of a size, e.g., about 4 mm, suitable for insertion through a puncture in the flesh of a living being, to a surgical site within the body, as will be described below. The proximal portion 22 of the sheath is fixed within a larger, shorter support sleeve 26, which in turn is supported for axial sliding movement within handle cavity 28 by rings 30, e.g., plastic. The rings engage the wall 29 of cavity 28 in a manner to allow sliding movement when actuation knob 32 is moved, but with sufficient force to resist inadvertent movement during normal use of the instrument. The handle, cap, shaft, sheath and sleeve are all metal, typically stainless steel.

Support sleeve 26 is connected by pin 34 to an actuation knob 32, disposed to slide generally axially along the outer surface of the handle. For this purpose, the pin 34 extends through a slot 36 defined in the wall of the handle. Sliding of the knob, e.g., by engagement of the user's thumb, causes axial movement of the sheath relative to the handle 12 and relative to blade 18. In this manner, the sheath 20 is adapted to move between a first position (FIG. 3), in which the distal portion 24 of sheath 20 surrounds the blade, e.g., to enable safe positioning of the instrument in the body without cutting, and a second, retracted position (FIG. 4) to expose the blade for cutting.

Referring to FIG. 2, circumferential movement of knob 32 at the distal end of slot 36 lodges pin 34 in circumferential slot extension 37. Compression force applied against spring 40 in this position serves to secure the sheath against accidental dislodgement from the blade-protecting position, e.g., during handling.

The sheath has an inner diameter, I, e.g., about 3 mm, selected, in combination with the dimensions of the shaft and blade, to permit the instrument to be disassembled by unthreading cap 14 from the proximal end of handle 12, and withdrawing the shaft 16 and supporting blade 18 through the sheath and handle. In this manner, a blade may be replaced during a surgical procedure, e.g., for a blade of different configuration, without removing the instrument sheath from the puncture opening in the body.

Referring to FIGS. 3 and 4, a surgical instrument of the invention is prepared by threading a blade 18 into the distal end 17 of shaft 16, with the shaft and cap 14 disassembled from the instrument 10. The cap and shaft supporting the blade are then reassembled with the instrument by sliding the shaft through the handle cavity, into the sheath. The knob 32 is slid distally, then circumferentially, to lodge pin 34 in slot extension 37, with the force of spring 40 holding the pin in place; this moves the sheath 20 to its distal position, surrounding and protecting the blade 18 during handling, and protecting the flesh against accidental cutting during percutaneous introduction into the living body.

After a puncture opening 42 is provided through the flesh 44 of a living body, into a cavity 46 of the body, e.g., within the joint of a knee, the distal portion 24 of sheath 20 is inserted through the puncture. According to the invention, the blade 18 at this point is disposed within the sheath 20, protecting the tissue within the cavity 46 against accidental cutting engagement with the blade 18. The surgeon, viewing through endoscope 48, positions the distal end of the sheath, containing the blade, immediately adjacent the tissue to be cut. Once the instrument is properly positioned, the surgeon disengages pin 34 from slot extension 37, by moving knob circumferentially, and slides the actuation knob 32 proximally, e.g., about 1.5 inches, thereby retracting sheath 20 and exposing the cutting blade 18. Since the position of the blade is fixed relative to the handle, and the blade does not move as the sheath is retracted, the blade is exposed precisely at the position where cutting is to take place, and undesired movement of the blade, and thus potential danger of accidental cutting of tissue other than at the desired location, is avoided.

The sheath 20 further serves as a cannula, remaining in position, through the flesh, as the surgeon, when desired, quickly removes the blade and shaft through the instrument and reintroduces a new blade (on the same or a different shaft) without removing the instrument from the body. The entire process can take only a few seconds. Also avoided is trauma inherent with multiple changes of instruments.

Other embodiments are within the following claims. For example, referring to FIG. 5, the proximal portion 50 of the sheath 20 is disposed in sleeve 52. Actuation knob 54 is fixedly connected (e.g., by threads 55) to an adjustment sleeve 56 constructed for rotation about the handle 12 by means of pins 58 fixed to the handle and engaged in an annular groove defined about the order surface of sleeve 56. Other pins 60, fixed to sleeve 56, engage in spiral slots defined in the outer surface of sleeve 52 joined to sheath 20, whereby rotation of knob 54 causes axial movement of the sheath between its first and second positions.

What is claimed is:

1. A surgical instrument for operating percutaneously in a living body comprising:
   an elongated hollow handle,
   a shaft having a proximal portion extending within and secured, during use, to said handle and a distal portion extending distally of said handle,
   surgical cutting means fixedly supported during use by the distal end of said shaft,
   a slidable tubular sheath having a distal portion extending distally of said handle, about said shaft, to the region of said cutting means, said sheath sized and constructed for introduction into the living body through a puncture opening in its flesh,
   means for moving said sheath axially relative to said handle between a first position in which the distal portion of said sheath surrounds said cutting means, enabling safe positioning of said instrument in the body without cutting, and a second, retracted position exposing said surgical cutting means, the position of said cutting means relative to said handle being fixed during movement of said sheath, and
   a proximal cap removably connected to said handle, said sheath and said handle defining an elongated passage extending axially the length of said instrument, and said shaft and said cutting means being sized relative to said passage through said sheath and said handle whereby, upon disassembly of said cap from said handle, said shaft and blade are adapted for removal proximally through said passage, while said sheath remains in said puncture opening in the flesh of the living body.

2. The surgical instrument of claim 1 wherein said means for moving said sheath axially relative to said handle comprises
   a knob disposed for movement relative to the outer surface of said handle, and
   engagement means extending through said handle into fixed engagement with the proximal portion of said sheath disposed within said handle,
   whereby movement of said knob relative to the outer surface of said handle results in movement of said sheath between said first and second positions.

3. The surgical instrument of claim 2 wherein said means for moving said sheath axially relative to said handle further comprises
   a sleeve sized and constructed for axial sliding movement within said handle, the distal portion of said sheath being fixedly connected to said sleeve, and said engagement means being disposed in a slot defined through said handle, between fixed connection to said knob and to said sleeve.

4. The surgical instrument of claim 2 wherein said knob is disposed for sliding movement generally axially along the outer surface of said handle.

5. The surgical instrument of claim 2 wherein said knob comprises an annular ring disposed to rotate without axial movement about said handle.

6. The surgical instrument of claim 2 further comprising means for positively retaining said sheath in said first position surrounding said cutting means.

7. The surgical instrument of claim 1 wherein the outer diameter of said sheath is of the order of about 4 mm.

8. The surgical instrument of claim 1 wherein the inner diameter of said sheath is of the order of about 3 mm, and said cutting means and said sheath are sized for passage therethrough.

9. The surgical instrument of claim 1 wherein said sheath has a proximal portion slidably disposed within said handle.

* * * * *